US010932797B2

(12) United States Patent
Thomas (10) Patent No.: US 10,932,797 B2
(45) Date of Patent: Mar. 2, 2021

(54) STROKE CATHETER FOR USE IN REVASCULARIZATION PROCEDURES AND METHOD OF USING SAME

(71) Applicant: Jeffrey E. Thomas, Hillsborough, CA (US)

(72) Inventor: Jeffrey E. Thomas, Hillsborough, CA (US)

( * ) Notice: Subject to any disclaimer, the term of this patent is extended or adjusted under 35 U.S.C. 154(b) by 73 days.

(21) Appl. No.: 15/560,603

(22) PCT Filed: Mar. 24, 2016

(86) PCT No.: PCT/US2016/023957
§ 371 (c)(1),
(2) Date: Sep. 22, 2017

(87) PCT Pub. No.: WO2016/154403
PCT Pub. Date: Sep. 29, 2016

(65) Prior Publication Data
US 2018/0049759 A1    Feb. 22, 2018

Related U.S. Application Data

(60) Provisional application No. 62/138,599, filed on Mar. 26, 2015.

(51) Int. Cl.
*A61B 17/22*   (2006.01)
*A61M 25/10*   (2013.01)
*A61M 25/00*   (2006.01)

(52) U.S. Cl.
CPC ........... *A61B 17/22* (2013.01); *A61M 25/007* (2013.01); *A61M 25/1011* (2013.01);
(Continued)

(58) Field of Classification Search
CPC .......... A61B 17/22; A61B 2017/22079; A61B 2017/22067; A61B 2017/22054;
(Continued)

(56) References Cited

U.S. PATENT DOCUMENTS 6,165,199 A    12/2000  Barbut
8,088,103 B2    1/2012  Teeslink et al.
(Continued)

FOREIGN PATENT DOCUMENTS

WO    2013123007 A1    8/2013

OTHER PUBLICATIONS

Negative pressure. (n.d.) American Heritage® Dictionary of the English Language, Fifth Edition. (2011). Retrieved Jan. 15, 2020 from https://www.thefreedictionary.com/negative+pressure (Year: 2011).*

(Continued)

*Primary Examiner* — Jenna Zhang
(74) *Attorney, Agent, or Firm* — Benesch, Friedlander, Coplan & Aronoff LLP (57) ABSTRACT

A method of removing vascular blockage includes providing a catheter system, comprising an outer catheter, a bypass catheter, and a guidewire. In the catheter system, the bypass catheter is slidably disposed within the outer catheter. The method includes positioning a distal end of the catheter system at a proximal end of an occlusion located within a vessel and moving the bypass catheter through the occlusion so that a medicated treatment solution may be delivered through the bypass catheter to an area of the brain or other tissue served by the vessel blocked by the occlusion. Both during and after the delivery of medicated treatment solution to the blocked part of the vessel with the bypass catheter, the physician may engage the occlusion with the perforated segment of the outer catheter so that a thrombolytic agent can be delivered at the occlusion to disintegrate it and then removing at least a portion of the occlusion from the vessel.

21 Claims, 8 Drawing Sheets

(52) U.S. Cl.
CPC ............... *A61B 2017/22034* (2013.01); *A61B 2017/22044* (2013.01); *A61B 2017/22054* (2013.01); *A61B 2017/22067* (2013.01); *A61B 2017/22079* (2013.01); *A61B 2017/22084* (2013.01); *A61M 25/104* (2013.01); *A61M 2025/0004* (2013.01); *A61M 2025/0042* (2013.01); *A61M 2025/1045* (2013.01); *A61M 2025/1052* (2013.01)

(58) Field of Classification Search
CPC ........... A61B 2017/22044; A61B 2017/22034; A61B 2017/22084; A61M 25/1011; A61M 2025/0042; A61M 2025/1052; A61M 2025/1045; A61M 2025/0004; A61M 25/007; A61M 25/104
See application file for complete search history.

(56) References Cited

U.S. PATENT DOCUMENTS

| | | | |
|---|---|---|---|
| 8,262,611 B2 | 9/2012 | Teeslink et al. | |
| 8,398,589 B2 | 3/2013 | Teeslink et al. | |
| 8,622,992 B2 | 1/2014 | Baxter et al. | |
| 9,017,285 B2 | 4/2015 | Teeslink et al. | |
| 9,526,863 B2 | 12/2016 | Baxter et al. | |
| 9,526,874 B2 | 12/2016 | Teeslink et al. | |
| 2002/0188276 A1* | 12/2002 | Evans | A61M 25/0021 604/509 |
| 2006/0200191 A1* | 9/2006 | Zadno-Azizi | A61M 25/104 606/200 |
| 2008/0275393 A1* | 11/2008 | Bonnette | A61B 17/22 604/102.01 |
| 2011/0282195 A1 | 11/2011 | Solar et al. | |
| 2014/0214002 A1* | 7/2014 | Lieber | A61M 25/1011 604/509 |
| 2017/0136220 A1 | 5/2017 | Teeslink et al. | |

OTHER PUBLICATIONS

Suction. (n.d.) American Heritage® Dictionary of the English Language, Fifth Edition. (2011). Retrieved Jan. 15, 2020 from https://www.thefreedictionary.com/suction (Year: 2011).*
The Extended European Search Report; dated Sep. 12, 2018; 7 pages.
Communication pursuant to Article 94(3) EPC issued in related European application No. 16769666.5 dated Jul. 4, 2019.

* cited by examiner

STROKE CATHETER FOR USE IN REVASCULARIZATION PROCEDURES AND METHOD OF USING SAME

CROSS-REFERENCE TO RELATED APPLICATIONS

This application claims priority from PCT Patent Application No. PCT/US16/23957 filed Mar. 24, 2016 and U.S. Provisional Patent Application No. 62/138,599 filed on Mar. 26, 2015, which are incorporated by reference herein in their entirety.

FIELD OF INVENTION

This application relates in general to a stroke catheter system and method for treating a bifurcation blockage or clot formed in a major cerebral vessel. Specifically, this application relates to a bypass catheter system that combines a clot trapping mechanism, an aspiration mechanism for retrieving clot debris and methods to bypass the clot in order to restore blood flow and prolong the patency of the patient's vessel.

BACKGROUND OF THE INVENTION

Thrombotic or embolic occlusion of a cerebral artery is often the cause of an ischemic or acute stroke event. It is often characterized by a sudden loss of circulation to an area of the brain resulting in the loss of specific neurologic function. The occlusion in the middle cerebral artery (MCA) or its branches is the most common type of anterior circulation infarct, accounting for about two thirds of all first strokes. Immediately following such an acute stroke, it may be necessary to reopen an occluded MCA, preferably within eight hours from the initial occlusion event. Manipulation of the endothelium of a cerebral blood vessel is preceded by adherence of platelets, which adhere to the site of injury, and subsequently release clotting factors that act as chemo attractants, both binding platelets together and provoking more clotting proteins from the blood. The result of this amplified mechanism (i.e., platelet aggregation and activation) is the accumulation of platelets and their binding together at the site as a "white thrombus," i.e. fibrin/platelet thrombus, which rapidly re-occludes the blood vessel. In this situation, a thrombolytic agent such as tPA will no longer be effective, as it has no activity against this different type of thrombus. Thus, conventional methods of removing occlusions in a blood vessel may not be adequate in all situations.

BRIEF SUMMARY

In an embodiment a catheter system for alleviating a vascular blockage is provided. The catheter system comprising an outer catheter having a proximal end, a distal end, a central lumen, a perforated segment, at least one inflatable balloon; a bypass microcatheter; and a guidewire. In the catheter system, the bypass microcatheter is slidably disposed within the outer catheter.

The method for removing a vascular blockage includes providing a catheter system comprising an outer catheter, a bypass catheter, wherein the bypass microcatheter is slidably disposed within the outer catheter, positioning a distal end of the catheter system at a proximal end of an occlusion in a vessel and inflating a balloon so that blood flow can be arrested proximal to the occlusion. Subsequently, a bypass mechanism is initiated by extending a bypass microcatheter distally through and beyond the occlusion into the vessel so that a first medicated treatment solution may be delivered through the bypass microcatheter to an area of the brain or other tissue served by the vessel. Concurrently, the method also includes positioning a perforated segment of the outer catheter proximal to or within the occlusion and delivering a second medicated solution at the occlusion in order to disintegrate the occlusion and subsequently removing portions of the removable occlusion through a lumen of the outer catheter.

In one embodiment a stroke catheter system for treating a vascular bifurcation blockage is provided. The catheter system comprising an outer catheter having at least one inflatable balloon, a first bypass microcatheter, a second bypass microcatheter, and at least one guidewire, wherein the first and the second bypass microcatheters are slidably disposed within the outer catheter and are extendable into bifurcating distal branches of a vessel.

A method for treating a vascular blockage in a bifurcating vessel includes a catheter system comprising an outer catheter, a first bypass microcatheter, a second bypass microcatheter, wherein the outer catheter includes a first inflatable balloon and a second inflatable balloon and a perforated segment, positioning a distal end of the outer catheter system beyond the occlusion and before a bifurcating vessel, inflating a first balloon beyond the occlusion, inflating a second balloon before the occlusion in such a way that inflated balloons stop the blood flow proximal to the occlusion thus segmentally trapping the occlusion between the first and the second inflated balloons, extending a first bypass microcatheter and a second bypass microcatheter into a first and a second distal bifurcating branches respectively to either maintain the patency of the vessels or to deliver medicated therapeutic solution(s). The method further includes delivering medicated solution through a perforated segment on the outer catheter at the locally trapped occlusion to disintegrate it and an aspirating mechanism effectuated by the central lumen of the outer catheter to remove the disintegrated clot debris.

DESCRIPTION OF THE DRAWINGS

The accompanying drawings, which are incorporated in and constitute a part of the specification, illustrate various example systems, methods, and so on, that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

FIG. 6 (a) is a side view of the single barrel catheter of FIG. 1a with the bypass catheter extending beyond the occlusion of FIG. 4.

FIG. 6 (b) is a side view of the double barrel catheter of FIG. 1b with the guide wires extending beyond the occlusion of FIG. 4.

FIG. 13 (a) is a side perspective view of a portion of the single barrel catheter of FIG. 1 with a narrowing distal end.

FIG. 13 (b) is a side perspective view of a portion of the single barrel catheter of FIG. 1 with a gradually tapering distal end.

DETAILED DESCRIPTION

A catheter system 10 may be introduced for example into a patient suffering from an ischemic stroke in order to restore blood flow to an occluded area of a cerebral blood vessel. Generally, the catheter system 10, as shown in FIG. 1, consists of a single barrel arrangement (FIG. 1a) having a tubular member 13 or a double barrel arrangement (FIG. 1b) of tubular members 13 and 14. In one embodiment, the catheter system 10 includes an outer catheter 12, a bypass microcatheter 23, at least one flow-arresting balloon 24-a, and a guidewire 11. In another embodiment the catheter system 10 includes an outer catheter 12, a first bypass microcatheter 23, a second bypass microcatheter 25, two inflatable/flow-arresting balloons 24-a and 24-b, and at least one guidewire 11a (shown in FIGS. 1b and 2). The catheter system 10 may be introduced into a vessel of a patient via an extracranial guide catheter (ECGC) 5 having a proximal end 4, a distal end 3, a single lumen 8, an inflation lumen 7 disposed marginally and at least a single flow-arresting balloon 6 capable of arresting forward flow of blood in the extracranial carotid or vertebral or other source artery.

Figure 2:
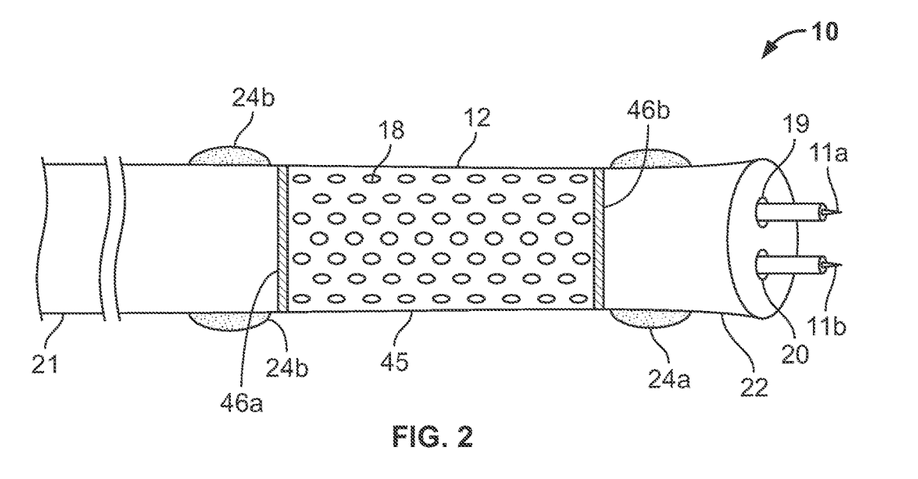
FIG. 2 is a side view of the proximal portion of the double barrel catheter of FIG. 1b.
Figure 5:
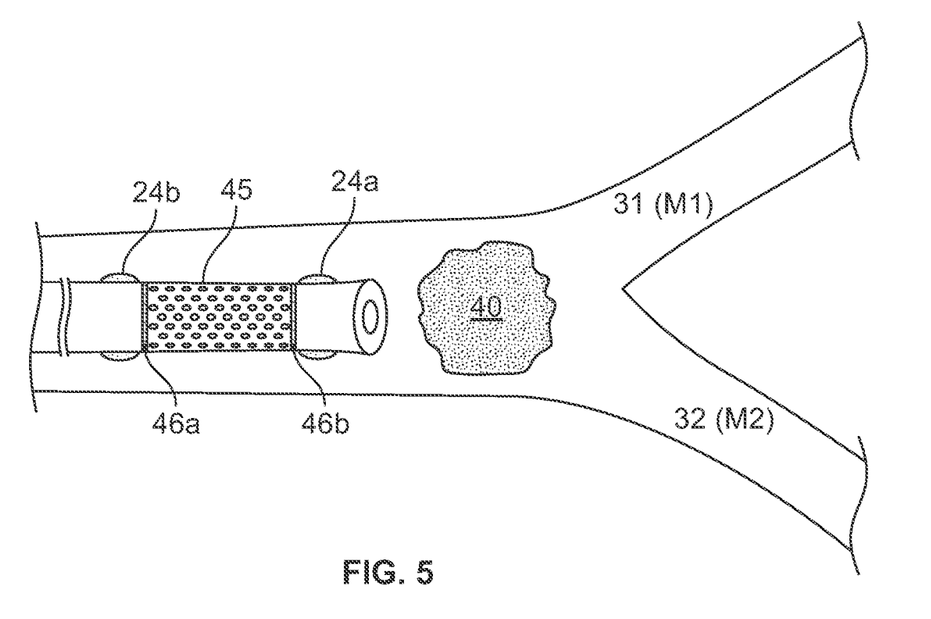
FIG. 5 is a side view of the single barrel catheter of FIG. 1 disposed proximal to the occlusion of FIG. 4.

The outer catheter 12 is generally tubular in shape and includes a first tubular barrel 13, a second tubular barrel 14, a proximal end 21, a transition portion (not shown), and a distal end 22. The first tubular barrel 13 and the second tubular barrel 14 may be formed integrally with, or affixed separately to, the outer catheter 12. Each of tubular barrel 13 and 14 include proximal open ends 16 and 17 and distal open ends 19 and 20, respectively. The outer catheter 12 may also include at least one inflatable flow-arresting balloon 24-a disposed on its proximal end 21, and at least one perforation 18 on the sidewall of the proximal end 21. Preferably, the sidewall portion of the proximal end 21 of outer catheter 12 may include plurality of perforations to form a substantially perforated segment/region 45 that may cover the proximal end 21 and/or distal end 22 and/or transition portions (FIG. 2). Radiographic markers 46-a and 46-b may be disposed on either side of the perforated segment 45 of the outer catheter 12 (shown in FIGS. 2 and 5).

Similar to the outer catheter 12, as shown in FIG. 1, the first bypass microcatheter 23 and second bypass microcatheter 25 may also include generally tubular bodies having proximal ends 26 and 27, respectively, transition portions (not shown), and distal ends 28 and 29, respectively. The outer catheter 12, first bypass microcatheter 23 and the second bypass catheter 25 each may include at least one lumen 15, 13' and 14' therein extending from the distal ends 22, 28, and 29 of the tubular bodies to the proximal ends 21, 26 and 27 of the tubular bodies (shown in FIG. 1b). However, only the lumen 13' and 14' of the first and second bypass microcatheters have open ends at both the proximal ends 26 and 27 and the distal ends 28 and 29, while the lumen 15 of the outer catheter 12 is open only at the proximal end 21 and may be closed at its distal end 22.

Figure 4:
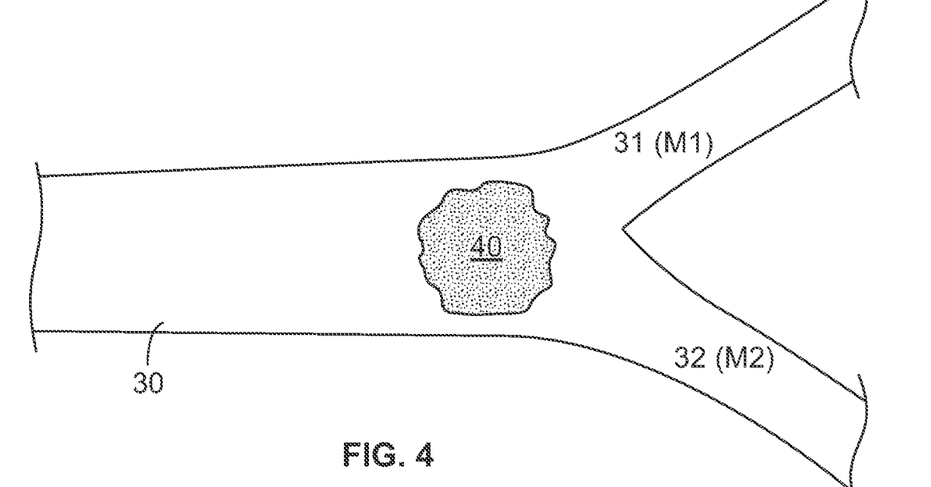
FIG. 4 is a side view of a cerebral vessel with bifurcating distal branches (M1 and M2) and an occlusion lodged near the junction of the bifurcation.

The first bypass catheter 23 and second bypass catheter 25 disposed within the first barrel 13 and the second barrel 14 of the outer catheter 12 are movable, rotatable in a clockwise/counterclockwise direction, or slidable in a forward/backward direction within the outer catheter 112 along a horizontal axis A. An inflation lumen 7 may be disposed marginally on at least the outer catheter 12 or one or both of the bypass microcatheters 23 and 25 respectively (shown in FIGS. 1d-g). The inflation lumen when filled with standard inflation fluid, such as saline or sterile water, may help to inflate one or more balloons present on the proximal portion of the outer catheter 12. To aid in the visualization of the first bypass microcatheter 23 and second bypass microcatheter 25 as they are navigated into the main vessel lumen 30, or within the lumen of the distal branches 31 (M1) and 32 (M2) (shown in FIG. 4), radiopaque markers 36-a, 36-b may be disposed on the distal portion of the first bypass microcatheter 23 and second bypass microcatheter 25 respectively (shown in FIG. 7).

For intracranial applications, such as an acute stroke, the outer catheter 12 may be made of flexible materials, including but not limited to, hypoallergenic silicone rubber, nitinol, nylon, polyurethane, polyethylene terephthalate (PETE), polyvinyl chloride (PVC), latex, titanium, stainless steel or thermoplastic elastomers or combinations thereof. Other suitable materials are also contemplated. The first bypass microcatheter 23 and the second bypass microcatheter 25 may be made of the same material as the outer catheter 12 or can be made from different material. The outer catheter 12 and the first bypass microcatheter 23 and second bypass microcatheter 25 may all have a hydrophilic surface coating. The first bypass microcatheter 23 and second bypass microcatheter 25 may have a length from about 150 cm to about 300 cm and may have an external diameter from about 0.62 mm to about 0.95 mm. In general, the internal diameter of outer catheter 12 is larger than the external diameter of first bypass microcatheter 23 and second bypass microcatheter 25. Ideally, the outer catheter 12 may have an internal diameter from about 0.10 mm to about 0.50 mm larger than the external diameter of the first and second bypass microcatheters 23 and 25 respectively.

The outer catheter 12, the first bypass microcatheter 23, and second bypass microcatheter 25 may all be color-coded or numerically coded to form a matching system. All catheters that can be used together should be similarly coded to avoid any mismatch.

Figure 3:
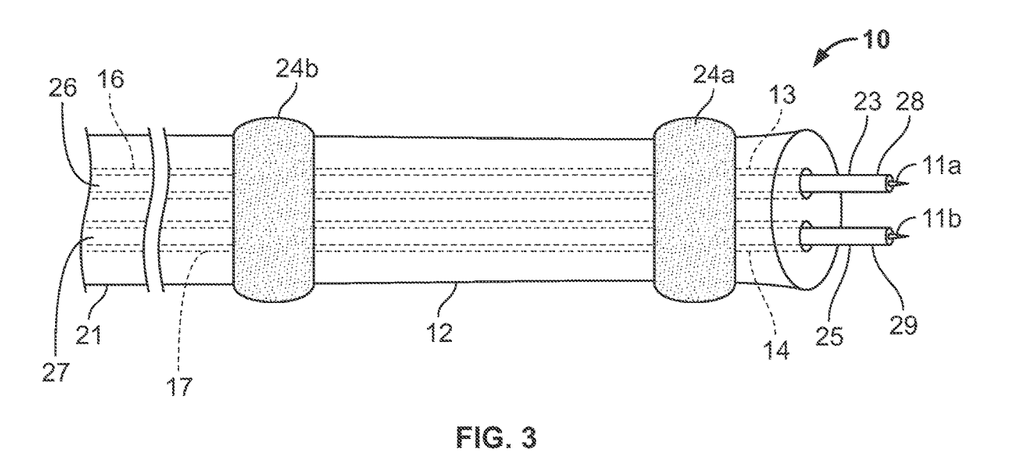
FIG. 3 is a side view of the double barrel catheter of FIG. 1 with two inflated balloons.

The catheter system 10 may also include one or more guidewires (shown in FIGS. 1-3). The primary guidewire 11 may be coated with a hydrophilic substance and may be used for initial placement of the catheter system 10. The primary guidewire 11 may have a length from about 180 cm to about 190 cm. A second and a third guidewire 11a and 11b, shown in FIGS. 6, 7 and 11-13, may also be used for navigating the first bypass microcatheter 23 or the second bypass microcatheter 25 and may be similarly constructed and have a length of about 300 cm.

Figure 1A:
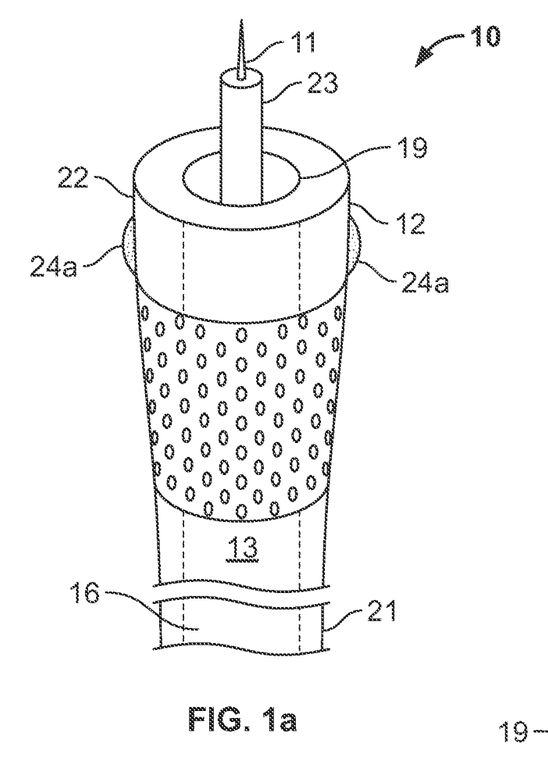
FIG. 1a is a side perspective view of a portion of a single barrel outer catheter.
Figure 1B:
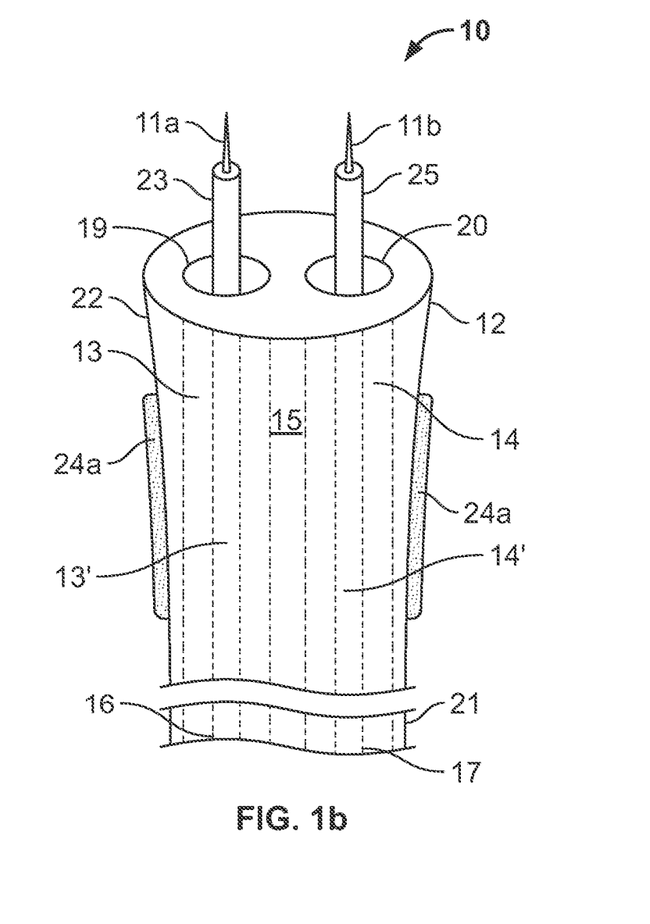
FIG. 1b is a side perspective view of a portion of a double barrel outer catheter.
Figure 1C:
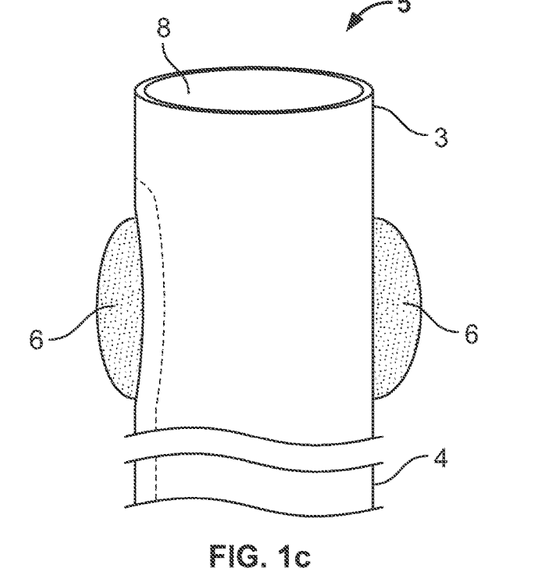
FIG. 1c is a side perspective view of an extracranial guide catheter (ECGC).
Figure 1D:
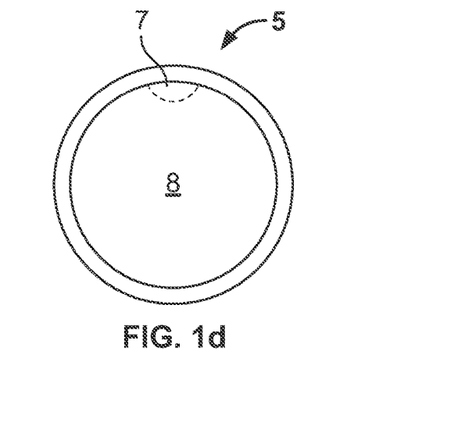
FIG. 1d-f are cross-sectional views of extracranial guide catheter (1d), a single barrel outer catheter (1e) and double barrel outer catheter (1f).
Figure 1E:
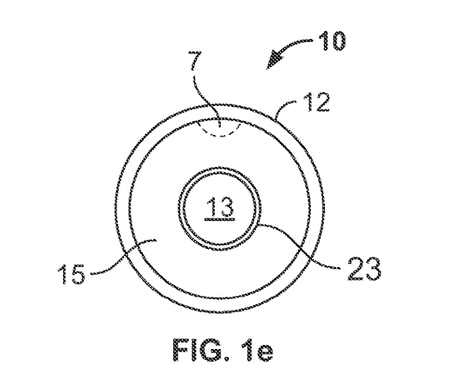
Figure 1F:
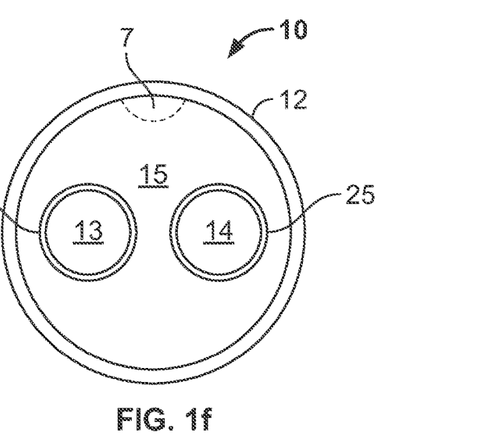
Figure 1G:
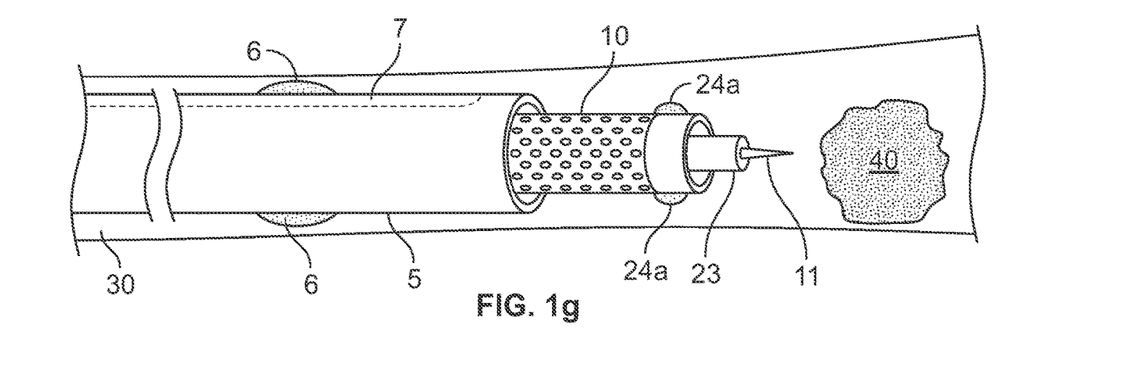
FIG. 1g is a side view of extracranial guide catheter, outer catheter and bypass microcatheter disposed at the site of an occlusion.
Figure 6A:
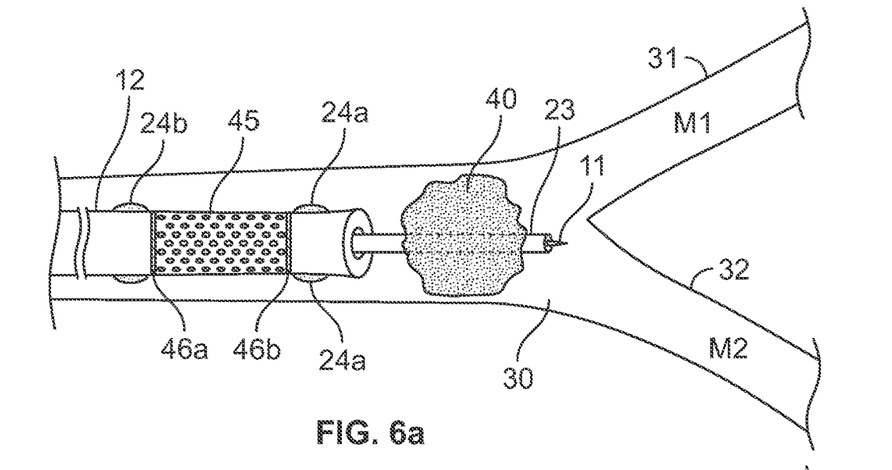
Figure 6B:
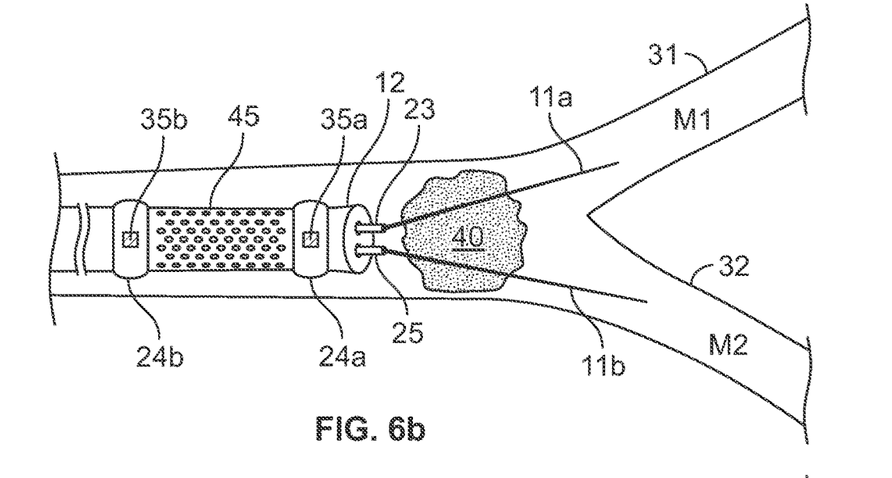

As shown in FIG. 1g, the catheter system 10 may be introduced into a patient's body by inserting a bi-lumen sheath (not shown) into the patient's femoral artery. The sheath may also include an extra channel for withdrawing arterialized blood. The catheter system 10, including the outer catheter 12, a bypass microcatheter 23 may then be, in the case of a stroke patient, navigated through the first lumen of the sheath into the femoral artery, up and around the arch of the aorta, into the carotid or vertebral artery, to the skull base, and deployed at the site of the arterial occlusion in the cerebral arteries. An intermediate guide catheter (ECGC) 5 that remains extracranial may also be deployed into the extracranial vertebral or carotid artery, serving then as the unmoving guide for the device, which then passes intracranially. The ECGC may be anchored in position by inflating the balloon 6 which may additionally serve to arrest blood flow in the vessel. A guidewire 11 may then be used to deploy the bypass microcatheter 23 which may then be extended through and beyond the occlusion as shown in FIG. 6a. Subsequently the physician may inflate a single balloon as shown in FIG. 6a or two balloons as shown in FIG. 6b, or a single balloon with a dumbbell shape, to arrest any trickling blood flow in the vessel beyond the flow arresting balloon 6 on the ECGC and proximal to occlusion. This flow arresting step may be performed prior to initiating the bypass mechanism and/or thrombolysis treatment.

It should be noted that while the outer catheter 12 and first bypass microcatheter 23 and second bypass microcatheter 25 are navigated through the body and positioned at the site of the occlusion as shown in FIG. 6b, pressurized (at approximately 300 mm Hg) and/or heparinized saline may be pumped from the proximal end 21 into the central lumen 15 and out through the perforations 18 of the outer catheter 12 at the site of occlusion 40. The heparinized saline may also be delivered beyond the occlusion 40 into distal branches M1 31 and M2 32 from the proximal ends 26 and 27 through lumen 13' and 14' of the first bypass microcatheter 23 and second bypass microcatheter 25 and out through the distal open ends 28 and 29, respectively. The influx of the heparinized saline through the catheters 12, 23 and 25 prevent blood and other potential debris, such as emboli, from entering and clogging the catheters. In one embodiment the first bypass microcatheter 23 and second bypass microcatheter 25 can be used to deliver other treatment solutions such a arterialized or oxygenated blood, thrombolytic agents, cold plasma, saline, etc.

Figure 7:
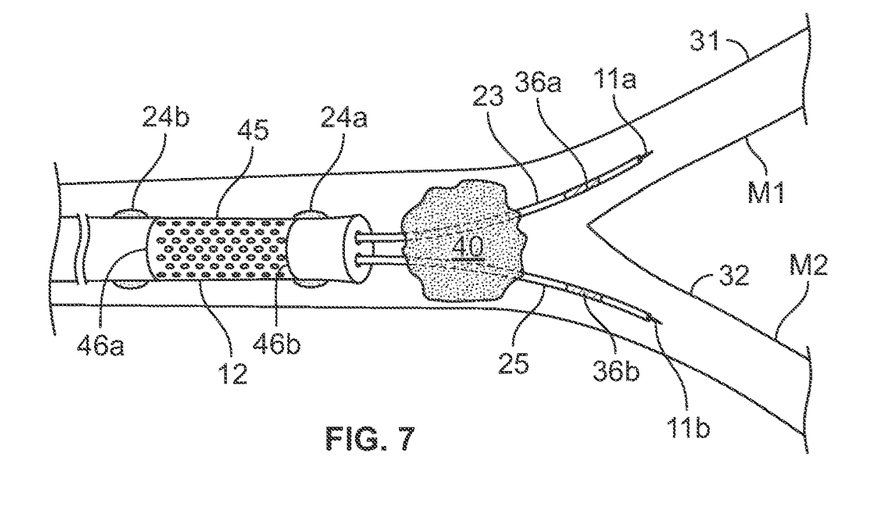
FIG. 7 is side view of the double barrel catheter with the first and second bypass microcatheters extending past the occlusion of FIG. 4.
Figure 8:
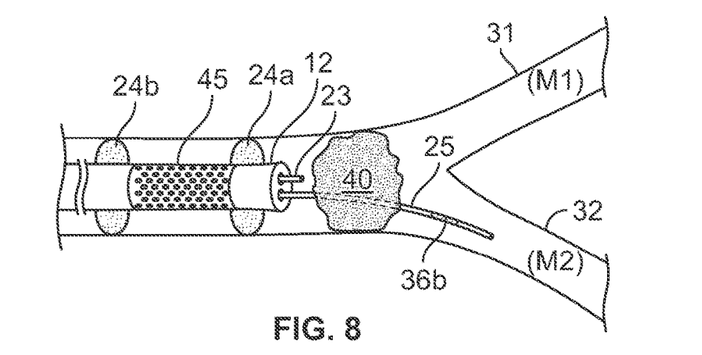
FIG. 8 is a side view of the double barrel catheter showing a partially withdrawn first bypass catheter positioned proximal to the occlusion site and the second bypass microcatheter extending into one of the distal branch M2.
Figure 9:
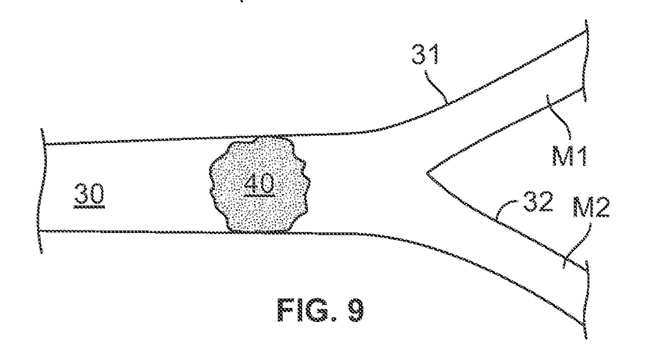
FIG. 9 is a side view of a cerebral vessel with an occluding clot lodged at a certain distance away from the bifurcating distal branches (M1 and M2).
Figure 10:
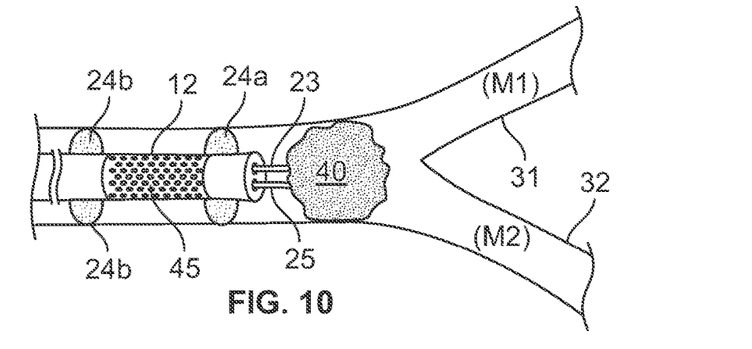
FIG. 10 is a side view of the proximal portion of the double barrel catheter positioned proximal to the occlusion of FIG. 9.

FIGS. 6-8 show the stroke catheter system 10 in successive positions in relation to an occlusion 40 lodged close to the junction of bifurcating branches in a main artery or vessel 30. FIGS. 6a and 6b show the outer catheter 12 positioned proximal to the occlusion 40 and guidewires 11a and 11b extended beyond the occlusion 40 and towards the distal branches M1 31 and M2 32. The radiopaque markers 36a and 36b disposed at the distal ends of the first bypass microcatheter 23 and the second bypass microcatheter 25 may further aid the physician to navigate both bypass microcatheters 23 and 25 towards the distal branches M1 31 and M2 32 (FIG. 7). This maneuver around or through the occlusion 40 as shown in FIG. 6 is possible due to the distensible nature of the vasculature tissue wall. Further, inflation of the balloon 24a and/or 24b allows the physician to not only lock the outer catheter 12 in position, it importantly serves to arrest blood flow in the vessel proximal to the occlusion (FIG. 8). Generally, the balloons 6, 24a and 24b, when fully inflated, can be at least about 3 mm in diameter and about 5 mm in length and are designed to sufficiently prevent the movement of the ECGC 5 and/or outer catheter 12 within the vessel wall and arrest blood flow at the site of occlusion 40. Design of the balloon may also be such as to enable inflation of two dumbbell ends separated by a more linear interposed section, through a single inflation channel. While all balloons are inflatable and capable of arresting forward flow of blood, the physician may choose to inflate only balloon, for example balloon 6 on the ECGC. In some instances the physician may opt to inflate two balloons, 6 and 24a or 24b or all the balloons disposed on the ECGC and outer catheter 12 to arrest forward flow of blood. Depending on the nature or fragility of the vessel wall the physician may also choose to inflate the balloons at different pressures in order to arrest blood flow.

Further, as shown in FIG. 8, since both bypass microcatheters 23 and 25 are movable within the outer catheter 12, the physician may choose to partially withdraw one of the bypass microcatheters. In doing so, the partially withdrawn bypass microcatheter can be positioned proximal to the occlusion 40 (as shown in FIG. 8) and may be used to deliver a thrombolytic agent at the occlusion 40 in addition to delivering the same thrombolytic agent through the perforated segment 45 of the outer catheter 12 to initiate the thrombolysis of the occlusion 40. Simultaneously, the other bypass microcatheter which is disposed within one of the distal branches M1 31 or M2 32 may be used to deliver arterialized blood or cold plasma to the portion of the brain (bypass mechanism) that has been deprived of oxygen due to the ischemic event thus restoring blood flow at least in one of the branches (FIG. 8).

Delivery of arterialized blood beyond the offending occlusion not only restores the life of at least one of the oxygen starved branching vessel even before the occlusion is removed, it importantly increases the amount of time the physician has to disintegrate the occlusion and reestablish the normal blood flow to the patient's ischemic brain. For example, the time taken to restore blood flow in the region distal to the occlusion using the catheter system 10 may be within 15 minutes, and preferably within 8 and 10 minutes after the procedure is initiated. Alternatively, an injection of arterialized blood with heparinized pressurized saline may be administered through the bypass microcatheter that extends into one of the branching vessels (second bypass microcatheter 25 in FIG. 8) by withdrawing the patient's own blood from the femoral artery into a syringe (not shown) and mixing the blood with heparinized saline.

After one of the bypass microcatheters is positioned to restore blood flow into one of the vessel branches M1 31 or M2 32 (as shown in FIG. 8), the physician may begin the thrombolysis treatment by pumping a thrombolytic agent through the partially withdrawn bypass microcatheter that is positioned proximal to the offending occlusion 40 (as shown by first bypass microcatheter 23 in FIG. 8). Delivery of thrombolytic agent at the occlusion may help to dissolve or disintegrate the occlusion 40. In addition, negative pressure may be applied via the central lumen 15 of the outer catheter 12. The pressure may be imparted by a negative-pressure pump or by the operator, using a syringe with a flow-limiting valve. The negative pressure generated will generally be less than the pressure required to collapse the walls of the involved blood vessel.

The negative pressure created in the central lumen 15 of the outer catheter can further help to aspirate the smaller clot debris via the perforations 18 of the outer catheter 12. The applied pressure also helps the larger debris that cannot pass through the perforations 18 to stick to the surface of the outer catheter 12. After the offending occlusion 40 is completely disintegrated, the delivery of the thrombolytic agent via the partially withdrawn bypass microcatheter 23 may be discontinued and the outer catheter 12 may be withdrawn with the clot debris adhered to its surface. Meanwhile, the second bypass microcatheter 25, as shown in FIG. 8, is allowed to deliver arterialized blood for an additional time of about 5 to 10 minutes before it may be removed.

Generally, both the first bypass microcatheter 23 and second bypass microcatheter 25 may extend up to 10 cm farther beyond the distal end of the outer catheter 12 in order to effectuate the bypass method and access the distal bifurcating branches of a vessel. In addition to the arterialized blood, thrombolytic agents, cold plasma, and saline may be administered past the occlusion in the manner described above. The cold plasma may be used to create regionalized hypothermia, extending the time the surgeon may have to effectively remove the obstructing clot.

Although in this embodiment the first bypass microcatheter 23 is shown to be partially withdrawn, and the second bypass microcatheter 25 is shown to deliver the arterialized blood to branch M2 32, it may be appreciated by one of ordinary skill in the art that the physician can choose to use either of the bypass microcatheters 23 and 25 as desired to deliver thrombolytic agent and arterialized blood. The physician may also choose to deliver medication directly to and within the thrombus by injecting it through the perforations now lodged within the occlusion.

In another embodiment, as shown in FIGS. 9-12, an offending occlusion lodged in the main vessel 30 at a certain distance from the junction of the bifurcating branches may be treated by an occlusion trapping mechanism that is effectuated by two inflated balloons.

Figure 11:
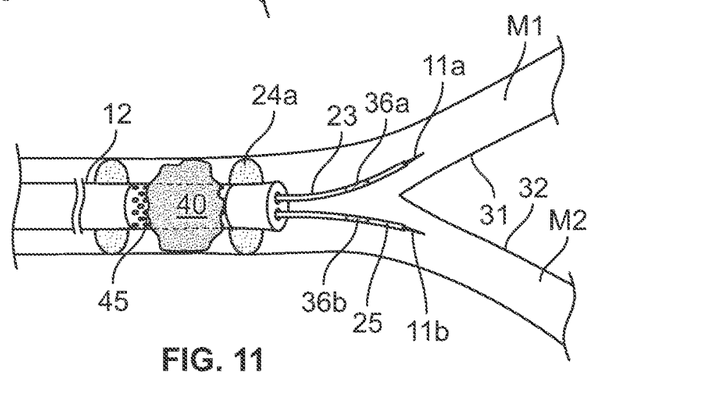
FIG. 11 is a side view of the double barrel catheter that is being extended through and beyond the occlusion of FIG. 9.
Figure 12:
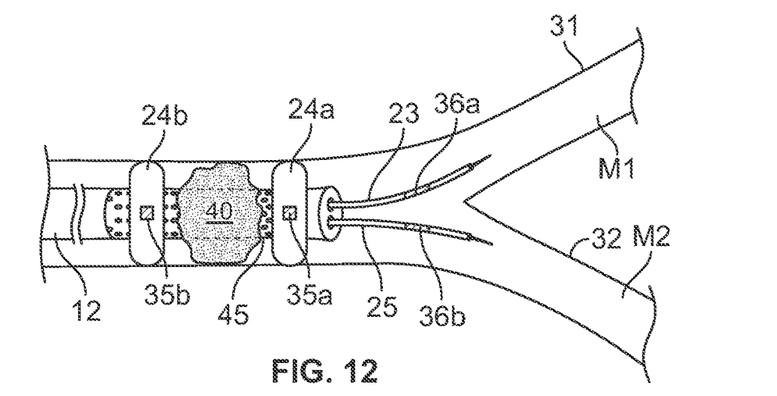
FIG. 12 is a side view of the double barrel catheter with a trapping mechanism deployed to trap the occlusion between the first and second inflated balloons.

In this embodiment, the outer catheter 12 is first navigated through and beyond the occlusion 40, as shown in FIG. 11, using one or two guidewires 11a and 11b until at least one of the balloons on the outer catheter 12, for example, balloon 24a in FIG. 12, is positioned beyond the occlusion 40, while the second balloon 24b is positioned proximal to the occlusion 40. The two balloons 24a and 24b are spaced on the outer catheter 12 in such a way that the distance between them is sufficient to arrest blood flow at the site of occlusion and trap occlusions that range in size from about 0.5 cm to about 3.0 cm in most cases of ischemia. The radiopaque markers 46a and 46b on either side of the perforated segment 45 on the outer catheter 12 (shown in FIG. 5) and/or the markers 35a and 35b on the balloons may further help the physician to visualize this maneuver. Once the occlusion 40 is positioned between the two balloons 24a and 24b, the balloons 24a and 24b may be inflated by delivering inflation fluid through an inflation lumen to create a segmental trap and/or a blood free zone. The inflated balloons 24a and 24b may also help to lock the outer catheter 12 in place. Importantly, inflating the balloons 24a and 24b on the outer catheter 12 stops blood flow in the vessel proximal to the occlusion so that a medicated solution can be delivered through the perforated region 45 on the outer catheter 12 to initiate thrombolysis of the occlusion 40 within the segmented region. Concurrently, the bypass mechanism may be initiated by extending the first bypass microcatheter 23 and second bypass microcatheter 25 into the distal branches M1 31 and M2 32 of the main vessel 30 with the help of the radiopaque markers 36a and 36b. In doing so the physician may pump a therapeutic solution, such as arterialized blood or cold plasma, through one or both of the bypass microcatheters 23 and 25 to restore blood flow in the regions of the brain beyond the occlusion 40 that is deprived of oxygen due to the ischemic event.

In this embodiment, the medicated solution includes, but not limited to, a thrombolytic agent or a platelet antagonist medication and may be delivered via the central lumen 15 and out through the perforated segment 45 of the outer catheter 12. Because the occlusion 40 is segmentally trapped and free of blood, the local concentration of the medication is sufficient to disintegrate the occlusion 40 in much less time than is required for an occlusion 40 when it is not segmentally trapped because of the localization of the medication and absence of dilution or washout effect. Once the occlusion is sufficiently disintegrated, the delivery of the medicated solution via the central lumen 15 of the outer catheter 12 is discontinued and a negative pressure is applied. The pressure applied helps to aspirate the smaller clot debris through the lumen 15 and allows larger debris to adhere to the surface of the outer catheter 12.

Because the bypass microcatheters 23 and 25 and the outer catheter 12 have separate and distinct lumina, the bypass microcatheters 23 and 25 may remain in place, while the outer catheter 12 is used to segmentally engage and remove at least a portion of the occlusion 40. As shown in FIGS. 8 and 12, once the catheter system 10 has been used to remove a portion of the occlusion 40, the bypass microcatheters 23 and 25 may be used to impart localized fluid-mediated hypothermia by delivering a pressurized cooling solution beyond the occlusion 40. The solution may generally include a heparinized pressurized saline and/or a blood/oxygenated compound that is delivered to produce localized regional hypothermia to the brain via the bloodstream. In this embodiment, the heparinized and pressurized saline component of the solution is cooled before it is introduced into the catheter system 10, either by itself or in combination with the oxygen-carrying compound (usually blood). It is contemplated that any suitable method of cooling the solution may be used, such as by a thermostat-controlled refrigeration device outside of the patient's body.

As shown in FIGS. 2, 5, 6-8, and 10-12, the distal end 22 of the outer catheter 12 includes a diffusion portion or perforated segment 45 having multiple perforations 18. The perforations 18 provide fluid communication from the lumen of the outer catheter 12 to the vessel wall 30. It is also contemplated that the perforations 18 may extend beyond the distal end 22 of the outer catheter 12 and in some embodiments the perforations 18 may be absent in regions where the balloons are disposed.

The radiographic markers that are disposed on either side of the perforated segment 45 or on the balloons 22 and 24 and in the distal ends of the bypass microcatheters 23 and 25 may include radiopaque rings or embedded pellets, among other suitable markers. Although it would be helpful to know a priori the length of the actual occlusion, not knowing the length does not limit the use of the stroke catheter system 10, as it can become known simultaneously with visualization of thrombosis using angiography.

Once the perforated segment 45 of the outer catheter 12 is positioned within the occlusion 40, the negative pressure being applied to the lumen of the outer catheter 12 can be discontinued so that a medicated treatment solution can be introduced again directly to the remaining occlusion 40 through the perforated segment 45 of the outer catheter 12. This system of localized, distributed administration of medication through the perforations 18 in the perforated segment 45 exposes a greater surface area of the target occlusion 40 to the medicated treatment solution, such as a thrombolytic agent, antiplatelet agent, or nitro-vasodilator (i.e. a nitric oxide-based medication). The localized delivery of thrombolytic agent, antiplatelet agent, or nitro-vasodilator through the perforated segment 45 will remove or reduce the size of the occlusion 40 by dissolution thereof in the case of the 2 former, or by increasing the size of the lumen of the occluded vessel 30 in the case of the latter, to improve blood flow there through.

In the case of administration of nitric oxide-based vasodilator, the effect is one of distributing vasodilator medication to a segment of occluded vessel, allowing localized vasodilation and helping to liberate the vessel wall from the occlusive thrombus by allowing it to expand away from the latter.

The perforated segment 45 may also be used to deliver intralesional medication, especially thrombolytic medication for dissolving the lesion, and/or vasodilator medication for increasing the width of the vessel 42 at the site of obstruction. The perforated segment 45 also may be used to deliver medication, such as antiplatelet (2B3A glycoprotein receptor blocker) or vasodilator medication, to a chosen segment of a blood vessel.

Figure 13A:
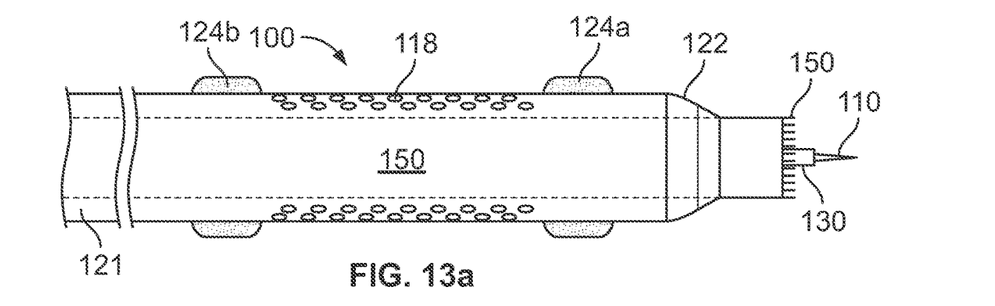
Figure 13B:
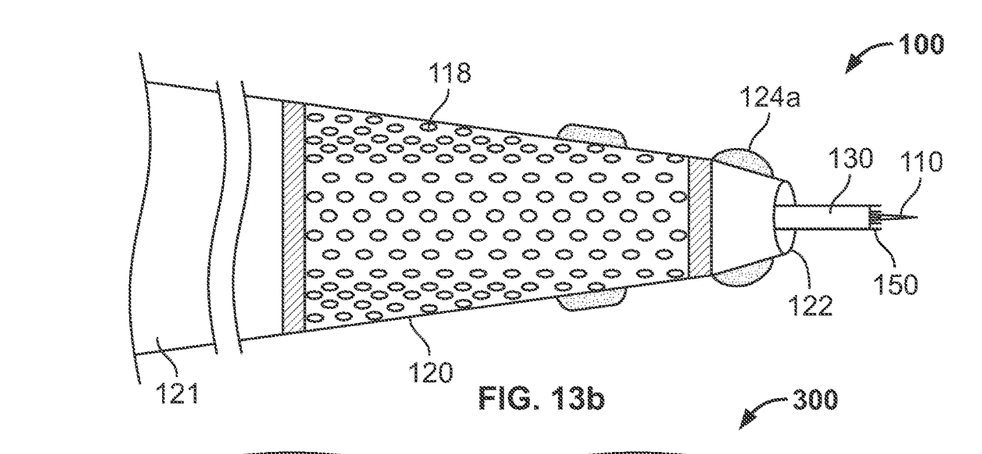

It is also contemplated that the catheter system 100 having a single bypass microcatheter can be tapered only at the distal end 122 as shown in FIG. 13a or can have a gradually tapering distal end as shown in FIG. 13b. In this embodiment, the outer catheter 120 has a single lumen 150 as shown in FIG. 13a to accommodate a bypass microcatheter 130. The bypass microcatheter 130 in this embodiment may be formed integrally with, or affixed separately to, the distal end of the distal portion 122 of the outer catheter 120. In some embodiments the distal end of the outer catheter 12 and/or bypass microcatheter 130 may include plurality of serrated teeth 150 that may help the physician to mechanically engage the occlusion 40 and break it up into smaller pieces (FIGS. 13a and 13b). In this embodiment, the bypass microcatheter 130 is affixed separately to the outer catheter 12 so that a rotational and/or clockwise or counter clockwise movement of the bypass microcatheter 130 will help a physician to mechanically cut through the occlusion 40. The serrated teeth may have a length of between 1.0 mm and about 4.0 mm and may also be retractable.

When the distal portion 122 of the outer catheter 120 is gradually tapered, the inner diameter of the distal end of the outer catheter 120 is only slightly larger than the outer diameter of the bypass catheter 130. Tapering the distal portion 122 of the outer catheter prevents fluid from exiting the distal end of the outer catheter 120, directing the flow of a medicament through the perforations 118.

Figure 14:
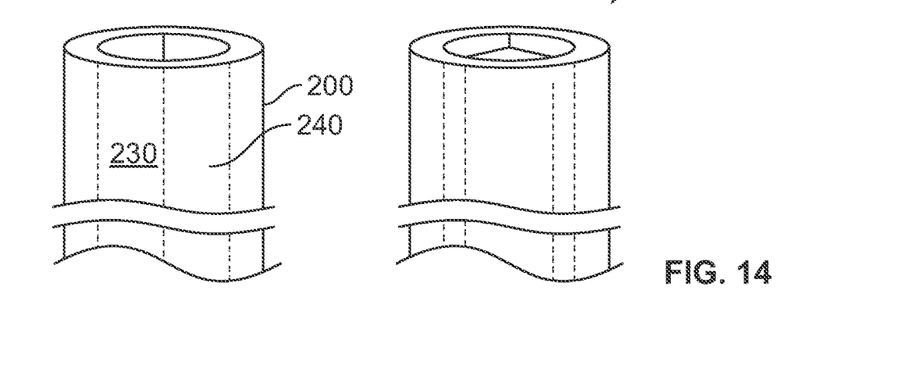
FIG. 14 (a & b) are side perspective views of an alternative embodiment of an outer catheter.

In another embodiment, the single lumen of the outer catheter 200 may have a diameter that is large enough to accommodate at least two bypass microcatheters 230 and 240 (FIG. 14). Other variations of the outer catheter as shown in FIG. 14 are also contemplated.

In addition, it is contemplated that the catheter system 10 may be used for both intracranial and peripheral (limb, ischemic bowel, organ ischemia) situations characterized by vascular insufficiency. One such embodiment may be used to treat cardiac ischemia, by insertion into a coronary artery and utilizing endovascular bypass, clot removal and localized medication delivery functions of the system. It may also be used in venous vasculature, for situations of venous obstruction or insufficiency.

Prophetic Example

A patient, a 62 year-old male, with recently diagnosed atrial fibrillation, presents to the emergency department with left-sided paralysis and slurred speech of two hours' duration.

Examination demonstrates an alert cooperative patient unable to move his left side. Cardiac rhythm is atrial fibrillation. Speech is coherent and dysarthric, with left facial droop. CTA demonstrates a right middle cerebral artery occlusion. Intravenous thrombolysis is initiated and a surgical team mobilized for neurointerventional treatment.

The patient is taken to the Interventional Neuroradiology O.R. and placed under general endotracheal anesthesia after informed consent is obtained. He is placed in a supine position on the operating table and scalp and limb electrodes are rapidly placed for intraoperative brain wave potential monitoring. The Micropuncture Seldinger technique is used for placement of the arterial sheath in the right femoral artery. The sheath is equipped with a side port that is in continuity with the lumen of the femoral artery, separate from the sheath aperture that transmits the guiding catheter. This port is utilized to provide arterial blood from the femoral artery for the bypass microcatheter. Interposed between the port and the proximal end of the bypass microcatheter is a means for diluting the femoral arterial blood with heparinized saline, and a means for cooling the arterialized blood in order to effect selective specific hypothermia, if desired.

An extracranial guide catheter of appropriate caliber (e.g., 6 Fr) is navigated over a hydrophilic guidewire (e.g., 0.035) through the femoral arterial sheath and through the descending aorta, thence over the aortic arch. The guide catheter is flushed while in the descending aorta in order to remove any residual air or thrombus before engaging the cerebral vasculature. The guide catheter is then positioned in the right common carotid artery; a roadmap image is then used to selectively deliver it into the Right internal carotid artery. Flow patency is checked and cerebral arterial injection is then performed using the 6 Fr catheter in two planes of view, which demonstrates and confirms the embolic occlusion of the right middle cerebral artery. The occlusion is located at the bifurcation of the vessel.

A catheter system as described above is then deployed into the occluded right middle cerebral artery through the guiding catheter, which is already in position. The system is navigated to the proximal side of the occlusion, which can be clearly visualized on an angiogram, as shown in FIG. 15.

Figure 15:
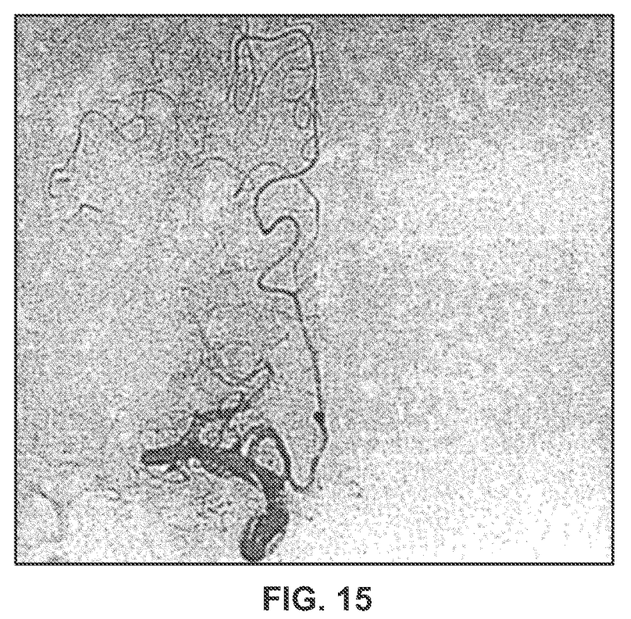
FIG. 15 is an angiogram showing an occlusion of the main barrel of the right middle cerebral artery including the bifurcation.
Figure 16:
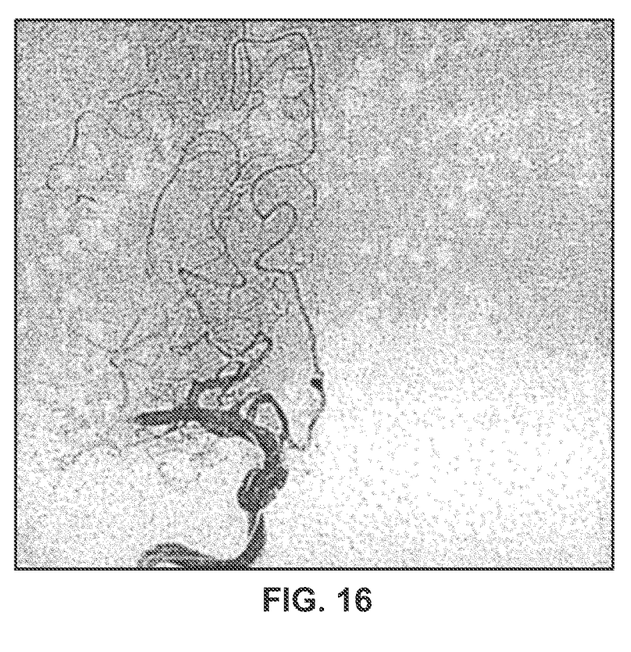
FIG. 16 is an angiogram showing partial revascularization of only one of the two branches.

(FIG. 15 showing occlusion of the main barrel of the Right middle cerebral artery including the bifurcation.)

An inner bypass catheter, slidably disposed within an outer catheter is then guided over the microguidewire into one of the occluded bifurcation branches, using fluoroscopy. The microguidewire is removed and microangiography is then performed through the microcatheter demonstrating the normal angiographic anatomy of that branch of the right middle cerebral artery. This microangiogram demonstrates that the bypass catheter is beyond the site of occlusion. The bypass catheter can now be used to deliver arterialized blood from the femoral artery of the patient, with or without dilution and cooling, or cooled saline alone, to the ischemic brain tissue distal to the occlusion.

Because the bifurcation of the middle cerebral artery is occluded, a single-barrel bypass will have only limited benefit; the branch that is not used to transmit the bypass (inner) catheter will remain occluded. The brain tissue in that distribution cannot be perfused with oxygenated blood and also cannot be treated with selective hypothermic neuroprotection (FIG. 2 showing partial revascularization of only 1 of 2 branches).

Therefore in this bifurcation embodiment of the stroke catheter a second inner bypass catheter is deployed over a microguidewire, into the second branch at the bifurcation. Microangiography through this second bypass microcatheter demonstrates that the second bypass microcatheter is now beyond the occlusion. Endovascular bypass is implemented as outlined above.

Now that the brain is protected from ischemia, more time may be taken to address the occlusive thrombus. This thrombus is characterized by particularly difficult physical characteristics (hard, organized, clot that had been present in the patient's left atrial chamber for an extended time, and that is resistant to ordinary intravenous thrombolysis) and a problematic physical location (at the bifurcation, it is not amenable to stent-based retrieval, which requires a branch selection, nor to simple aspiration, because it is hard, organized thrombus).

In this situation selective thrombolysis may be implemented by delivering thrombolytic medication to the proximal edge of the occlusion (where the main barrel of the device, and its perforations, is located), and delivering thrombolytic medication through the perforations directly to the clot. In this situation, it is not necessary to inflate the distal balloon, and may be more hazardous to do so because the branch vessels may be significantly smaller than the main trunk of the middle cerebral artery. Because blood flow has been interrupted at this level, however, thrombolytic medication will tend to stay in the area of the clot for a physically concentrated and prolonged impact, similar to having the segment isolated between balloons. These factors contribute to enhanced thrombolytic efficacy.

As the thrombolytic gradually digests the clot, the perforated segment may be moved gradually forward to engage the clot more internally and aggressively, right up to the bifurcation. During selective delivery of thrombolytic medication, the slidably disposed bypass catheter(s) remain in bypass position in order to continue brain protection. In this way the prolonged time exposure and highly concentrated, specifically-directed thrombolytic that are required to dissolve this particularly resistant thrombus are achieved, without compromising the protection of ischemic neurons (death rate approximately 2 million per minute in large vessel occlusion: Saver, et al. 2009).

In addition, more thrombolytic agent may be administered within the remaining occlusive clot by retracting either of the two bypass catheters toward the level of the perforations, at variable distances within the remaining thrombus, and delivering thrombolytic agent through the bypass catheter into the clot. During such a maneuver, the bypass function of that particular microcatheter is interrupted. The slidably disposed bypass microcatheter can be returned to distal bypass position at any time.

Effectiveness of the intervention may be monitored by observing return or improvement in intraoperative neurophysiologic monitoring parameters, and periodic microangiography demonstrating bypass patency.

The perforations may also be used to periodically aspirate the proximal portion of the occlusion to which they have access, removing clot debris if possible. The possibility of ultimate escape of smaller clot fragments into the distal branches once the system has been removed remains if thrombolysis is only partially successful, but smaller fragments create lesser occlusions and are also more amenable to subsequent thrombolytic therapy. Since much smaller doses of thrombolytic medication are required using this device (because of specific concentrated delivery and minimized wastage into the general circulation), there remains considerable therapeutic margin for delivery of more medication following the surgical procedure.

Once it has been decided to terminate the intervention (based on time elapsed and demonstration of improved brain electrical potentials, as well as microangiography from the proximal side of the occlusion), the distal perforations may be finally aspirated while withdrawing the device. This will enhance aspiration of lysed particulate material and also entrapment of larger particles against the device wall as the device is withdrawn. Prior to withdrawal of the device, it is helpful to inflate the balloon on the extracranial guide catheter (ECGC). This maneuver halts blood flow in the extracranial carotid or vertebral source artery, and decreases the likelihood that any entrapped clot particles that are being withdrawn are liberated and carried forward into the intracranial circulation.

While example methods and compositions have been illustrated by describing examples, and while the examples have been described in considerable detail, it is not the intention of the applicant to restrict or in any way limit the scope of the appended claims to such detail. It is, of course, not possible to describe every conceivable combination of components or methodologies for purposes of describing the systems, methods, devices, and so on, described herein. Additional advantages and modifications will readily appear to those skilled in the art. Therefore, the invention is not limited to the specific details, the representative revascularization catheter system 10, and illustrative examples shown and described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

What is claimed is:

1. A catheter system for alleviating vascular blockage comprising:

an outer catheter having a proximal portion, a distal portion, a central lumen, a perforated region comprising at least one perforation, one or more inflatable balloons disposed on the outer catheter, wherein the at least one perforation of the perforated region is disposed between a first inflatable balloon of the one or more inflatable balloons and the proximal portion;

a bypass catheter having a bypass lumen with an open proximal end and an open distal end, wherein the bypass catheter is slidably disposed within the outer catheter, and wherein the bypass catheter is configured to extend through and beyond the distal portion of the outer catheter and further through an occlusion located within a blood vessel, and is configured to transmit fluid through the open distal end;

an inflation lumen configured to inflate the one or more inflatable balloons;

first pumping means for imparting a negative pressure in the central lumen of the outer catheter, and;

second pumping means for pumping a thrombolytic agent or other fluid into the bypass lumen at the open proximal end, and further through the bypass lumen fully from the open proximal end toward and outward through the open distal end.

2. The catheter system of claim 1, wherein the perforated region of the outer catheter is flanked by radiographic markers.

3. The catheter system of claim 1, wherein the bypass catheter is a microcatheter.

4. The catheter system of claim 1, wherein the one or more inflatable balloons arrest blood flow when inflated.

5. The catheter system of claim 1, wherein the first pumping means comprises a negative pressure pump attached to a proximal end of the outer catheter.

6. The catheter system of claim 1, wherein the inflation lumen is disposed marginally on the outer catheter.

7. The catheter system of claim 1, further comprising a guide catheter configured to guide the outer catheter into a vessel lumen.

8. The catheter system of claim 1, comprising a second bypass catheter, wherein the second bypass catheter comprises a central lumen and an open distal end and the second bypass catheter is capable of transmitting fluid through the open distal end and is slidably disposed within the outer catheter.

9. The catheter system of claim 8, wherein the second bypass catheter is configured to extend through and beyond the occlusion.

10. The catheter system of claim 1, wherein the outer catheter is configured to navigate through and beyond the occlusion.

11. The catheter system of claim 1, wherein the negative pressure aspirates at least a portion of clot debris through the perforated region of the outer catheter.

12. The catheter system of claim 1, wherein the negative pressure allows at least a portion of clot debris to adhere to a surface of the outer catheter.

13. The catheter system of claim 1, wherein the first pumping means comprises a syringe that is configured to impart the negative pressure.

14. The catheter of system of claim 1, wherein the first pumping means comprises a flow-limiting valve.

15. The catheter system of claim 1, wherein the one or more inflatable balloons comprise the first inflatable balloon and a second inflatable balloon, and the perforated region is disposed between the first inflatable balloon and the second inflatable balloon.

16. A catheter system for alleviating vascular blockage comprising:
a pair of balloons;
an outer catheter upon which the pair of balloons are mounted, the outer catheter having a distal end, an inflation lumen, a central lumen, and a perforated segment with perforations communicating the central lumen with an exterior of the outer catheter between the pair of balloons;
a first fluid in the central lumen at the perforated segment of the outer catheter, wherein the first fluid has a negative pressure relative to the exterior of the outer catheter between the pair of balloons;
a bypass catheter extending within the central lumen and outward through the distal end of the outer catheter, wherein the bypass catheter has a bypass lumen with an outlet spaced distally from the distal end of the outer catheter; and
a second fluid in the bypass lumen, wherein the second fluid has a positive pressure relative to the negative pressure of the first fluid.

17. The catheter system of claim 16, wherein the outlet is an open distal end of the bypass catheter.

18. The catheter system of claim 16, further comprising a guide wire extending through the bypass catheter.

19. A catheter system for alleviating vascular blockage, comprising:
an outer catheter having a central lumen with an open distal end, an inflation lumen, and a diffusion portion including a perforated segment of the outer catheter, whereby the outer catheter is configured to take a deployed position with the perforated segment adjacent to a clot in a blood vessel;
an inflatable balloon disposed on the outer catheter in communication with the inflation lumen between the open distal end and the perforated segment; and
a bypass catheter extending within the central lumen, through the perforated segment of the outer catheter, and outward through the open distal end of the central lumen, wherein the bypass catheter has a bypass lumen with an open distal end, and is free of a perforation that communicates the bypass lumen with the central lumen within the perforated segment of the outer catheter, whereby fluid in the bypass lumen can bypass the clot for delivery to a location spaced distally from outer catheter when the outer catheter is in the deployed position.

20. The catheter system of claim 19, further comprising first pumping means for imparting a negative pressure in the central lumen in the outer catheter, and second pumping means for pumping a thrombolytic agent or other fluid into the bypass lumen in the bypass catheter.

21. The catheter system of claim 20, wherein the second pumping means is configured to function simultaneously with the first pumping means.

* * * * *